US011439532B2

(12) United States Patent
Velis (10) Patent No.: US 11,439,532 B2
(45) Date of Patent: Sep. 13, 2022

(54) POINT OF DELIVERY COLD SLURRY GENERATION

(71) Applicant: MIRAKI INNOVATION THINK TANK LLC, Cambridge, MA (US)

(72) Inventor: Christopher Velis, Cambridge, MA (US)

(73) Assignee: MIRAKI INNOVATION THINK TANK LLC, Cambridge, MA (US)

( * ) Notice: Subject to any disclaimer, the term of this patent is extended or adjusted under 35 U.S.C. 154(b) by 1197 days.

(21) Appl. No.: 15/946,410

(22) Filed: Apr. 5, 2018

(65) Prior Publication Data

US 2018/0289537 A1 Oct. 11, 2018

Related U.S. Application Data

(60) Provisional application No. 62/482,003, filed on Apr. 5, 2017.

(51) Int. Cl.
| | | |
|---|---|---|
| A61F 7/00 | (2006.01) | |
| A61F 7/12 | (2006.01) | |
| A61K 9/00 | (2006.01) | |
| A61K 47/02 | (2006.01) | |
| A61M 25/10 | (2013.01) | |
| A61K 47/10 | (2017.01) | |

(52) U.S. Cl.
CPC ............ *A61F 7/123* (2013.01); *A61F 7/0085* (2013.01); *A61K 9/0019* (2013.01); *A61K 47/02* (2013.01); *A61F 2007/0057* (2013.01); *A61F 2007/0095* (2013.01); *A61F 2007/126* (2013.01); *A61K 47/10* (2013.01); *A61M 25/1011* (2013.01); *A61M 2025/105* (2013.01); *A61M 2025/1013* (2013.01); *A61M 2205/3368* (2013.01); *A61M 2205/362* (2013.01); *A61M 2205/3606* (2013.01); *A61M 2205/366* (2013.01)

(58) Field of Classification Search
CPC .............................. A61B 18/0218; A61F 7/12
USPC ........................................................ 607/105
See application file for complete search history.

(56) References Cited

U.S. PATENT DOCUMENTS

| | | |
|---|---|---|
| 3,373,906 A | 3/1968 | Hart et al. |
| 3,893,834 A | 7/1975 | Armstrong |
| 4,619,678 A | 10/1986 | Rubin |
| 4,966,601 A | 10/1990 | Draenert |
| 4,983,045 A | 1/1991 | Taniguchi |
| 4,986,079 A | 1/1991 | Koseki et al. |
| 5,143,063 A | 9/1992 | Fellner |
| 5,304,128 A | 4/1994 | Haber et al. |
| 5,445,523 A | 8/1995 | Fischer et al. |
| 5,507,790 A | 4/1996 | Weiss |
| 5,769,879 A | 6/1998 | Richards et al. |
| 6,032,675 A | 3/2000 | Rubinsky |
| 6,041,787 A | 3/2000 | Rubinsky |
| 6,067,803 A | 5/2000 | Wolsey et al. |
| 6,244,052 B1 | 6/2001 | Kasza |
| 6,300,130 B1 | 10/2001 | Toner et al. |
| 6,324,863 B1 | 12/2001 | Henry |
| 6,334,328 B1 | 1/2002 | Brill |
| 6,403,376 B1 | 6/2002 | Toner et al. |
| 6,413,444 B1 | 7/2002 | Kasza |
| 6,428,563 B1 | 8/2002 | Keller |
| 6,430,957 B1 | 8/2002 | Inada et al. |
| 6,458,109 B1 | 10/2002 | Henley et al. |
| 6,475,212 B2 | 11/2002 | Dobak, III et al. |
| 6,547,811 B1 | 4/2003 | Becker et al. |
| 6,575,930 B1 | 6/2003 | Trombley, III et al. |
| 6,673,607 B2 | 1/2004 | Toner et al. |
| 6,849,072 B2 | 2/2005 | Lee et al. |
| 6,962,601 B2 | 11/2005 | Becker et al. |
| 7,118,591 B2 | 10/2006 | Frank et al. |
| 7,276,051 B1 | 10/2007 | Henley et al. |
| 7,367,341 B2 | 5/2008 | Anderson et al. |
| 7,389,653 B2 | 6/2008 | Kasza et al. |
| 7,422,601 B2 | 9/2008 | Becker et al. |
| 7,507,234 B2 | 3/2009 | Utley et al. |
| 7,588,547 B2 | 9/2009 | Deem et al. |
| 7,603,868 B2 | 10/2009 | Sveinsson |
| 7,681,411 B2 | 3/2010 | DiLorenzo |
| 7,713,266 B2 | 5/2010 | Elkins et al. |
| 7,854,754 B2 | 12/2010 | Ting et al. |
| 8,117,854 B2 | 2/2012 | Lampe et al. |
| 8,192,474 B2 | 6/2012 | Levinson |

(Continued)

FOREIGN PATENT DOCUMENTS

| | | |
|---|---|---|
| CN | 102271741 | 12/2011 |
| CN | 102307545 | 1/2012 |

(Continued)

OTHER PUBLICATIONS

Ash, 2003, Chronic peritoneal dialysis catheters: overview of design, placement, and removal procedures, Int Nephrol Dialysis 16(4):323-34.

Brink, 2008, Abdominoplasty with direct resection of deep fat, Plast Reconstructive Surg 123(5):1597-1603.

Ding, 2008, The association between non-subcutaneous adiposity and calcified coronary plaque: A substudy of the multi-ethnic study of atherosclerosis, Am J Clin Nutr 88(3):645-650.

(Continued)

*Primary Examiner* — Raymond J Henley, III
(74) *Attorney, Agent, or Firm* — Wenderoth, Lind & Ponack, L.L.P.

(57) ABSTRACT

The present invention provides methods and devices for making a cold slurry at a point of delivery. A point of delivery device delivers cold slurry components to a location at or near a target tissue. The components are combined to form the cold slurry at or near the point of delivery. This approach to generating a cold slurry at the point of delivery allows the characteristics of the cold slurry, such as temperature, particle shape and particle size, to be maintained and controlled.

19 Claims, 9 Drawing Sheets

(56) References Cited

U.S. PATENT DOCUMENTS

| | | |
|---|---|---|
| 8,275,442 B2 | 9/2012 | Allison |
| 8,285,390 B2 | 10/2012 | Levinson et al. |
| 8,298,216 B2 | 10/2012 | Burger et al. |
| 8,308,681 B2 | 11/2012 | Slocum et al. |
| 8,337,539 B2 | 12/2012 | Ting et al. |
| 8,505,315 B2 | 8/2013 | Kasza et al. |
| 8,523,927 B2 | 9/2013 | Levinson et al. |
| 8,535,275 B2 | 9/2013 | Salzman |
| 8,603,073 B2 | 12/2013 | Allison |
| 8,608,696 B1 | 12/2013 | DiMeo et al. |
| 8,676,338 B2 | 3/2014 | Levinson |
| 8,702,774 B2 | 4/2014 | Baker et al. |
| 8,808,241 B2 | 8/2014 | DiMeo et al. |
| 8,840,608 B2 | 9/2014 | Anderson et al. |
| 8,974,451 B2 | 3/2015 | Smith |
| 9,044,212 B2 | 6/2015 | LePivert |
| 9,078,634 B2 | 7/2015 | Gonzales et al. |
| 9,132,031 B2 | 9/2015 | Levinson et al. |
| 9,314,368 B2 | 4/2016 | Allison et al. |
| 9,345,526 B2 | 5/2016 | Elkins et al. |
| 9,375,345 B2 | 6/2016 | Levinson et al. |
| 9,398,930 B2 | 7/2016 | Leung et al. |
| 9,408,745 B2 | 8/2016 | Levinson et al. |
| 9,522,031 B2 | 12/2016 | Anderson et al. |
| 9,545,523 B2 | 1/2017 | Nanda |
| 9,585,687 B2 | 3/2017 | Tenenbaum et al. |
| 9,649,220 B2 | 5/2017 | Anderson et al. |
| 9,655,770 B2 | 5/2017 | Levinson et al. |
| 9,656,056 B2 | 5/2017 | Boyden et al. |
| 9,980,765 B2 | 5/2018 | Avram et al. |
| 10,174,985 B2 | 1/2019 | Arnitz et al. |
| 10,406,021 B2 | 9/2019 | Wu et al. |
| 10,500,342 B2 | 12/2019 | Velis |
| 2001/0005338 A1 | 6/2001 | Muhlbauer et al. |
| 2002/0107199 A1 | 8/2002 | Walker |
| 2003/0012079 A1 | 1/2003 | Coffeen et al. |
| 2003/0032996 A1 | 2/2003 | Hallman |
| 2003/0074903 A1 | 4/2003 | Upadhye et al. |
| 2003/0171715 A1 | 9/2003 | Hommann et al. |
| 2003/0220674 A1 | 11/2003 | Anderson et al. |
| 2004/0073280 A1 | 4/2004 | Dae et al. |
| 2004/0092883 A1 | 5/2004 | Casey et al. |
| 2004/0092920 A1 | 5/2004 | Rozenshpeer |
| 2004/0199115 A1 | 10/2004 | Rosenman |
| 2004/0220559 A1 | 11/2004 | Kramer et al. |
| 2005/0203598 A1 | 9/2005 | Becker et al. |
| 2005/0251120 A1 | 11/2005 | Anderson et al. |
| 2006/0030843 A1 | 2/2006 | Lane et al. |
| 2006/0036302 A1 | 2/2006 | Kasza et al. |
| 2006/0122673 A1 | 6/2006 | Callister et al. |
| 2006/0161232 A1 | 7/2006 | Kasza et al. |
| 2006/0190066 A1 | 8/2006 | Worthen |
| 2007/0010861 A1 | 1/2007 | Anderson et al. |
| 2007/0056313 A1 | 3/2007 | Kasza et al. |
| 2007/0106247 A1 | 5/2007 | Burnett et al. |
| 2007/0198071 A1 | 8/2007 | Ting et al. |
| 2007/0255362 A1 | 11/2007 | Levinson et al. |
| 2007/0270925 A1 | 11/2007 | Levinson |
| 2008/0045880 A1 | 2/2008 | Kjeken et al. |
| 2008/0077201 A1 | 3/2008 | Levinson et al. |
| 2008/0077202 A1 | 3/2008 | Levinson |
| 2008/0077211 A1 | 3/2008 | Levinson et al. |
| 2008/0161772 A1 | 7/2008 | Nayak et al. |
| 2008/0195114 A1 | 8/2008 | Murphy |
| 2008/0236186 A1 | 10/2008 | Kasza et al. |
| 2008/0287839 A1 | 11/2008 | Rosen et al. |
| 2008/0300540 A1 | 12/2008 | Lewis |
| 2009/0012497 A1 | 1/2009 | Uber, III et al. |
| 2009/0018623 A1 | 1/2009 | Levinson et al. |
| 2009/0018624 A1 | 1/2009 | Levinson et al. |
| 2009/0018625 A1 | 1/2009 | Levinson et al. |
| 2009/0018626 A1 | 1/2009 | Levinson et al. |
| 2009/0018627 A1 | 1/2009 | Levinson et al. |
| 2009/0030366 A1 | 1/2009 | Hoch |
| 2009/0071829 A1 | 3/2009 | O'Banion et al. |
| 2009/0118722 A1 | 5/2009 | Ebbers et al. |
| 2009/0125087 A1 | 5/2009 | Becker et al. |
| 2009/0149929 A1 | 6/2009 | Levinson et al. |
| 2009/0255276 A1 | 10/2009 | Kasza et al. |
| 2009/0270814 A1 | 10/2009 | Masi et al. |
| 2010/0036295 A1 | 2/2010 | Altshuler et al. |
| 2010/0081971 A1 | 4/2010 | Allison |
| 2010/0152824 A1 | 6/2010 | Allison |
| 2010/0152880 A1 | 6/2010 | Boyden et al. |
| 2010/0249753 A1 | 9/2010 | Gaisser et al. |
| 2010/0274184 A1 | 10/2010 | Chun |
| 2010/0280582 A1 | 11/2010 | Baker et al. |
| 2010/0308257 A1 | 12/2010 | Lampe et al. |
| 2010/0312202 A1 | 12/2010 | Henley et al. |
| 2011/0066216 A1 | 3/2011 | Ting et al. |
| 2011/0190751 A1 | 8/2011 | Ingle et al. |
| 2011/0238050 A1 | 9/2011 | Allison et al. |
| 2011/0238051 A1 | 9/2011 | Levinson et al. |
| 2011/0300079 A1 | 12/2011 | Martens et al. |
| 2012/0000217 A1 | 1/2012 | Gudnason |
| 2012/0022518 A1 | 1/2012 | Levinson |
| 2012/0055187 A1 | 3/2012 | Raines et al. |
| 2012/0167878 A1 | 7/2012 | Belzon et al. |
| 2012/0203312 A1 | 8/2012 | Batzer et al. |
| 2012/0239123 A1 | 9/2012 | Weber et al. |
| 2012/0289761 A1 | 11/2012 | Boyden et al. |
| 2013/0066309 A1 | 3/2013 | Levinson |
| 2013/0079684 A1 | 3/2013 | Rosen et al. |
| 2013/0116758 A1 | 5/2013 | Levinson et al. |
| 2013/0116759 A1 | 5/2013 | Levinson et al. |
| 2013/0158440 A1 | 6/2013 | Allison |
| 2013/0158636 A1 | 6/2013 | Ting et al. |
| 2013/0190744 A1 | 7/2013 | Avram et al. |
| 2013/0245731 A1 | 9/2013 | Allison |
| 2013/0253496 A1 | 9/2013 | Anderson et al. |
| 2013/0319080 A1 | 12/2013 | Sezaki et al. |
| 2014/0005760 A1 | 1/2014 | Levinson et al. |
| 2014/0067025 A1 | 3/2014 | Levinson et al. |
| 2014/0091113 A1 | 4/2014 | Brewster et al. |
| 2014/0200511 A1 | 7/2014 | Boyden et al. |
| 2014/0257443 A1 | 9/2014 | Baker et al. |
| 2014/0277219 A1 | 9/2014 | Nanda |
| 2014/0277302 A1 | 9/2014 | Weber et al. |
| 2014/0303608 A1 | 10/2014 | Taghizadeh |
| 2014/0303696 A1 | 10/2014 | Anderson et al. |
| 2014/0303697 A1 | 10/2014 | Anderson et al. |
| 2014/0316393 A1 | 10/2014 | Levinson |
| 2014/0358079 A1 | 12/2014 | Fischell et al. |
| 2014/0378937 A1 | 12/2014 | Anderson et al. |
| 2015/0090769 A1 | 3/2015 | Lotsch |
| 2015/0112195 A1 | 4/2015 | Berger et al. |
| 2015/0141916 A1 | 5/2015 | Albrecht et al. |
| 2015/0216816 A1 | 8/2015 | O'Neil et al. |
| 2015/0297246 A1 | 10/2015 | Patel et al. |
| 2015/0320938 A1 | 11/2015 | King et al. |
| 2015/0328077 A1 | 11/2015 | Levinson |
| 2015/0342780 A1 | 12/2015 | Levinson et al. |
| 2015/0343156 A1 | 12/2015 | Fischell et al. |
| 2016/0051401 A1 | 2/2016 | Yee et al. |
| 2016/0058956 A1 | 3/2016 | Cohn et al. |
| 2016/0081974 A1 | 3/2016 | Lee et al. |
| 2016/0089550 A1 | 3/2016 | DeBenedictis et al. |
| 2016/0112195 A1 | 4/2016 | Jochheim et al. |
| 2016/0128767 A1 | 5/2016 | Azamian et al. |
| 2016/0175141 A1 | 6/2016 | Wu et al. |
| 2016/0184568 A1 | 6/2016 | Harris et al. |
| 2016/0242661 A1 | 8/2016 | Fischell et al. |
| 2016/0317621 A1 | 11/2016 | Bright |
| 2016/0354137 A1 | 12/2016 | Fischell et al. |
| 2016/0354237 A1 | 12/2016 | Gonzales et al. |
| 2017/0035603 A1 | 2/2017 | Kammer et al. |
| 2017/0051353 A1 | 2/2017 | Eng |
| 2017/0105869 A1 | 4/2017 | Frangineas, Jr. |
| 2017/0136237 A1 | 5/2017 | Eckhouse et al. |
| 2017/0143538 A1 | 5/2017 | Lee et al. |
| 2017/0164965 A1 | 6/2017 | Chang et al. |
| 2017/0202613 A1 | 7/2017 | Pellegrino et al. |
| 2017/0246032 A1 | 8/2017 | Gonzales et al. |
| 2017/0274011 A1 | 9/2017 | Garibyan et al. |

(56) References Cited

U.S. PATENT DOCUMENTS

| | | |
|---|---|---|
| 2017/0274078 A1 | 9/2017 | Garibyan et al. |
| 2017/0325992 A1 | 11/2017 | DeBenedictis et al. |
| 2018/0008500 A1 | 1/2018 | Anderson et al. |
| 2018/0116868 A1 | 5/2018 | Velis et al. |
| 2018/0140514 A1 | 5/2018 | Velis et al. |
| 2018/0289538 A1 | 10/2018 | Velis |
| 2018/0311079 A1 | 11/2018 | Garibyan et al. |
| 2019/0053939 A1 | 2/2019 | Garibyan et al. |
| 2019/0054242 A1 | 2/2019 | Velis |
| 2020/0046552 A1 | 2/2020 | Velis et al. |
| 2020/0086054 A1 | 3/2020 | Velis |
| 2020/0113627 A1 | 4/2020 | Alas et al. |
| 2020/0114041 A1 | 4/2020 | Alas et al. |

FOREIGN PATENT DOCUMENTS

| | | |
|---|---|---|
| CN | 103110473 A | 5/2013 |
| CN | 104010598 | 8/2014 |
| CN | 105640706 A | 6/2016 |
| EP | 0418979 A2 | 3/1991 |
| EP | 0 445 951 | 9/1991 |
| ES | 2 421 545 | 9/2013 |
| GB | 2 338 428 | 12/1999 |
| JP | 2003-500097 | 1/2003 |
| JP | 2008-529663 | 8/2008 |
| JP | 2009-539575 | 11/2009 |
| WO | 2006/086479 | 8/2006 |
| WO | 2009/086399 A2 | 7/2009 |
| WO | 2009/089090 | 7/2009 |
| WO | 2013/036540 | 3/2013 |
| WO | 2013/113970 | 8/2013 |
| WO | 2016/033380 A1 | 3/2016 |
| WO | 2016/033384 A1 | 3/2016 |
| WO | 2016/054165 | 4/2016 |
| WO | 2016/090175 A1 | 6/2016 |
| WO | 2016/138045 | 9/2016 |
| WO | 2017/196548 A1 | 11/2017 |
| WO | 2018/187573 A1 | 10/2018 |

OTHER PUBLICATIONS

Fox, 2007, Abdominal visceral and subcutaneous adipose tissue compartments—association with metabolic risk factors in the Framingham heart study, Circulation 116:39-48.
Garaulet, 2006, Relationship between fat cell size and number and fatty acid composition in adipose tissue from different fat depots in overweight/obese humans, Int J Obes 30(6):899-905.
Gradinger, 2005, Abdominoplasty, Chapter 83, pp. 2935-3026, in The art of aesthetic surgery: principles & techniques, Nahai, Ed., Quality Med Pub, St. Louis Mo. (92 pages).
International Search Report & Written Opinion dated Aug. 29, 2018 for PCT/US2018/026273 (15 pages).
International Search Report and Written Opinion dated Apr. 12, 2011, for PCT/US11/24766, filed Feb. 14, 2011 (11 pages).
International Search Report and Written Opinion dated May 7, 2018, for PCT/US18/20387, filed Mar. 1, 2018 (7 pages).
International Search Report and Written Opinion dated Jun. 11, 2018, for PCT/US2018/026260, filed Apr. 5, 2018 (6 pages).
Laven, 2006, A pilot study of ice-slurry application for inducing laparoscopic renal hypothermia, BJU Int 99:166-70.
Laverson, 2006, Improving abdominoplasty results: reconstruction of the linea alba sulcus by direct excision, Aesthetic Surg J 26:682-6.
Stevens, 2014, Does cryolipolysis lead to skin tightening? A first report of cryodermadstringo, Aesth Surg J 34(6):NP32-NP34.
Yamamoto, 2010, Adipose depots possess unique developmental gene signatures, Obesity 18(5):872-78.
Extended European Search Report dated Dec. 9, 2020 in European Application No. 18781693.9.
Search Report and Written Opinion dated Feb. 17, 2021 in Singapore Application No. 11201909303T, with English translation.
Search Report and Written Opinion dated Feb. 8, 2021 in Singapore Application No. 11201909305P, with English translation.
International Search Report and Written Opinion dated May 7, 2018, for PCT/US2018/20387, filed Mar. 1, 2018 (7 pages).
Int Search Report & Written Op dated June 11, 2018, for PCT/US2018/026260, filed April 5, 2018 (6 pages)
Esposito, 2016, Do you know this syndrome? Type 2 benign symmetric lipomatosis (Launois-Bensaude), Brazilian Annals of Dermatology 91:841.
Gentile, 2016, Lipodystrophy in Insulin-Treated Subjects and other Injection-Site Skin Reactions: Are we Sure Everything is Clear?, Diabetes Therapy 7.
International Preliminary Report on Patentability dated Aug. 21, 2012, for International application No. PCT/US2011/024766, filed Feb. 14, 2011 (8 pages).
Int Search Report & Written Op dated Dec. 11, 2019, for PCT/US2019/054828, filed Oct. 4, 2019 (8 pages).
Int Search Report & Written Op dated Dec. 23, 2019, for PCT/US2019/054834, filed Oct. 4, 2019 (10 pages).
Int Search Report & Written Op dated Feb. 11, 2020, for PCT/US2019/055633, filed Oct. 10, 2019 (12 pages).
Int Search Report & Written Op dated Jan. 2, 2020, for PCT/US2019/055605, filed Oct. 10, 2019 (9 pages).
International Search Report and Written Opinion dated May 15, 2018, for PCT/US2017/059947, filed Nov. 3, 2017 (8 pages).
Kanamori, 2015, "A case of an 8-year-old boy who was strongly suspected of suffering from familial angiolipomatosis", J Pediatric Surg 3.
Kosseifi, 2010, "Dercum's Disease: An Unusual Presentation", Pain Medicine 11:1432.
Lv, 2017, "A review of the postoperative lymphatic leakage", Oncotarget 8:69069.
Popescu, 2014, "Proteus Syndrome: a difficult diagnosis and management plan", J Med and Life 7:1.
Extended European Search Report dated Dec. 16, 2020 in European Application No. 18781069.2.
Extended European Search Report dated Aug. 28, 2020 in European Application No. 17868153.2.
Written Opinion dated Jul. 1, 2020 in Singapore Application No. 11201903946S.
Office Action dated Mar. 1, 2021 in Chinese Application No. 2017800786800, with English translation.

POINT OF DELIVERY COLD SLURRY GENERATION

CROSS REFERENCE TO RELATED APPLICATIONS

This application claims the benefit under 35 U.S.C. § 119(e) of U.S. Provisional Application Ser. No. 62/482,003 filed on Apr. 5, 2017, the entire disclosure of which is incorporated herein by reference.

BACKGROUND

Cold slurries used in medical applications typically comprise a partially frozen saline solution. Cold slurries are used in surgical applications to induce therapeutic hypothermia and slow organ and tissue metabolic rates thereby protecting a patient's organs during a surgical procedure. Cold slurries can also be injected into a patient for selective or non-selective cryotherapy and/or cryolipolysis.

Approaches to preparing and delivering a cold slurry to fat tissue through a cannula or needle are reported in International Application No. PCT/US2015/047292; U.S. patent application Publication No. 2013/0190744; and U.S. Provisional Application No. 62/416484, which are incorporated by reference herein in their entirety. An injectable cold slurry typically can have particle sizes ranging from 0.1 millimeters to 1.5 millimeters. The particles are generally globular in shape giving the cold slurry high fluidity. This allows the slurry to flow easily through a small diameter needle. In contrast, an ice slush consisting of dendritic crystals is difficult to inject without clogging.

A traditional approach to making an injectable cold slurry is to mix a saline solution with ice, crush it, and condition it prior to injection. The resulting cold slurry is then transferred to a syringe for injection. There are many challenges with this approach, including maintaining temperature, shape, and size of the cold slurry particles. As the slurry warms, the particles lose the desired shape and size. The problem of melting cold slurry is further exacerbated when a large amount of cold slurry needs to be delivered to many different areas. By the time the last injection of cold slurry is made, the cold slurry is markedly different than when first injected. Refreezing the cold slurry is not an option because doing so causes dendritic crystals to form that may clog the syringe needle.

SUMMARY

The present invention provides methods and devices for making a cold slurry at a point of delivery. A point of delivery device delivers cold slurry components to a location at or near a target tissue. The components are combined to form the cold slurry at or near the point of delivery. This approach to generating a cold slurry at the point-of-delivery allows the characteristics of the cold slurry, such as temperature, particle shape and particle size, to be maintained and controlled Point of delivery generation also allows cold slurry to be made on demand and on a continuous basis. This is particularly useful for treatment over an extended period of time during which melting can occur. The point of care, just-in-time slurry delivery of the invention delivers fresh cold slurry over an entire course of treatment obviating concerns over melting and slurry decomposition. The invention can also greatly reduce the cost and time associated with making cold slurry in batches.

One aspect of the invention comprises methods of making a cold slurry at or near a target tissue. Preferred methods include delivering components needed to make a cold slurry. A first component can be water or a water mixture, such as water and glycerol. Cold slurry is formed at or near the target tissue as a result of interaction between the components. The delivery of components for making a cold slurry; and the formation of a cold slurry can occur continuously so that there is steady supply of fresh cold slurry at or near the target tissue.

Preferred ingredients for forming a cold slurry include liquid water and solid water. A surfactant, such as glycerol, can be added as well to enhance the fluidity of the cold slurry. Liquid water and the solid water are mixed to form a cold slurry at or near the target tissue. The solid water can be broken into particles that are mixed with the liquid water to form the slurry. Solid water (i.e., ice) can also be formed from another supply of liquid water that is subsequently frozen within the device.

The cold slurry can also be made at or near the target tissue from the nucleation of supercooled water with ice pellets (seeds). In this case the supercooled water is purified liquid water that has been "undercooled" below the freezing point of water. The supercooled water remains in liquid form due, in part, to its purity. When the supercooled water interacts with the ice pellets, it crystallizes and forms the cold slurry.

Methods of the invention are carried out using a point of delivery generation device. An exemplary device includes a first cannula for delivering a first component and a second cannula for delivering a second component to a target tissue. The first and second cannulas can be arranged side-by-side such that their respective outlets are more or less aligned to facilitate cold slurry formation. In some examples, the first and second cannulas each have a size and shape suitable for inserting through the subject's skin.

Cold slurry can also be made at or near a target tissue using a balloon. In a preferred embodiment, the balloon comprises an outer balloon and an inner balloon. The inner balloon is filled with liquid water supplied through, for example, a first delivery cannula. A space between the inner balloon and the outer balloon is filled with a cooling fluid or gas supplied through a second delivery cannula. This causes a cold slurry to form inside the inner balloon. The inner balloon can optionally be punctured (e.g., by a puncturing needle on the device) to release the cold slurry at or near the target tissue. In this example of the point of delivery generation device, the first delivery cannula and the second delivery cannula are arranged coaxially. The invention may also include a temperature sensor to measure the temperature of the cold slurry made at or near the target tissue. Other factors and aspects of the invention are provided in the following detailed description thereof.

BRIEF DESCRIPTION OF DRAWINGS

FIG. 4 is a view of a generating end of a point of delivery generation device for forming solid water from a first supply of liquid water and then forming a cold slurry from the solid water and a second supply of liquid water and .

DETAILED DESCRIPTION

Methods and devices of the invention comprise elements for point-of-care delivery of cold slurry to a tissue or organ. The invention obviates the need to pre-mix slurry prior to delivery, thus ensuring that fresh slurry (i.e., uncrystallized and at appropriate phase and temperature) is delivered for the duration of treatment and uniformly to all treatment areas. In a preferred embodiment, slurry is made in situ at a point of delivery in a patient. Components (reactants) used to generate the slurry are provided under conditions that result in the formation of a slurry at an appropriate temperature and of an appropriate consistency for a desired treatment protocol. In a highly-preferred embodiment, methods of the invention are provided subcutaneously to adipose tissue in order to cause reduction of the adipose tissue. Methods and devices of the invention can also be applied to cause reduction of visceral fat, or to reduce pain.

Figure 1:
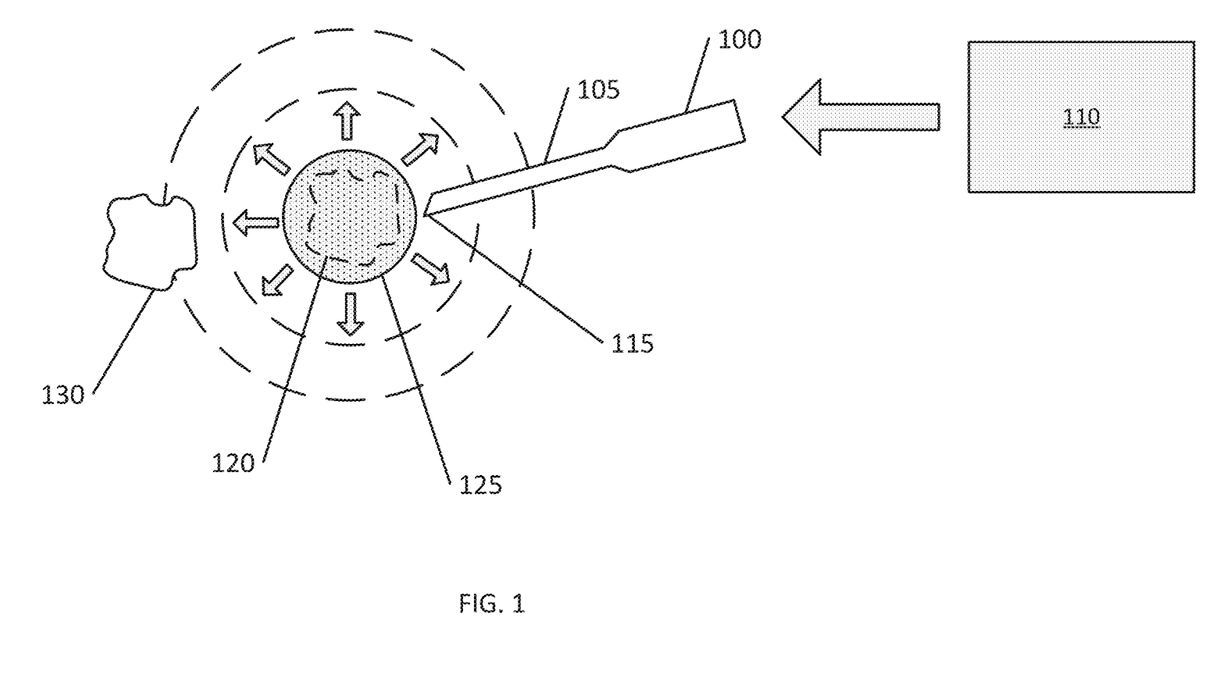
FIG. 1 is a diagram of an approach to generating a cold slurry inside a patient's body.

FIG. 1 shows an example of a point of delivery generation device 100 for making a cold slurry inside a patient's body. The device 100 includes an application cannula 105 having a shape and size configured to be inserted through a patient's skin. The device 100 is fluidly coupled to a supply 110 providing components for making a cold slurry. At the distal of the application cannula 105, there is a generating end 115 for forming a cold slurry from the components.

The point of delivery generation device 100 is used by inserting the application cannula 105 through the patient's skin and advancing the generating end 115 to a location at or near a target tissue or treatment site 120 (shown in phantom line). The target tissue 120 can, for example be subcutaneous adipose tissue. The cold slurry ingredients, such as liquid water, solid water, and glycerol, are pumped or otherwise conveyed, separately, from the supply 110, through the application cannula 105, and out the generating end 115. At the generating end 115, the components interact with each other and form the cold slurry 125 at or near the target tissue 120.

The cooling effect of the cold slurry 125 is localized to the target tissue 120 and possibly surrounding tissue, such as adjacent tissue 130. In this way, discomfort caused by the cold treatment is limited. The cold slurry is sterile and biocompatible; and, as such, the cold slurry 125 can be advantageously left in the body (e.g. no removal of the slurry is necessary after cooling has been effected).

Figure 2:
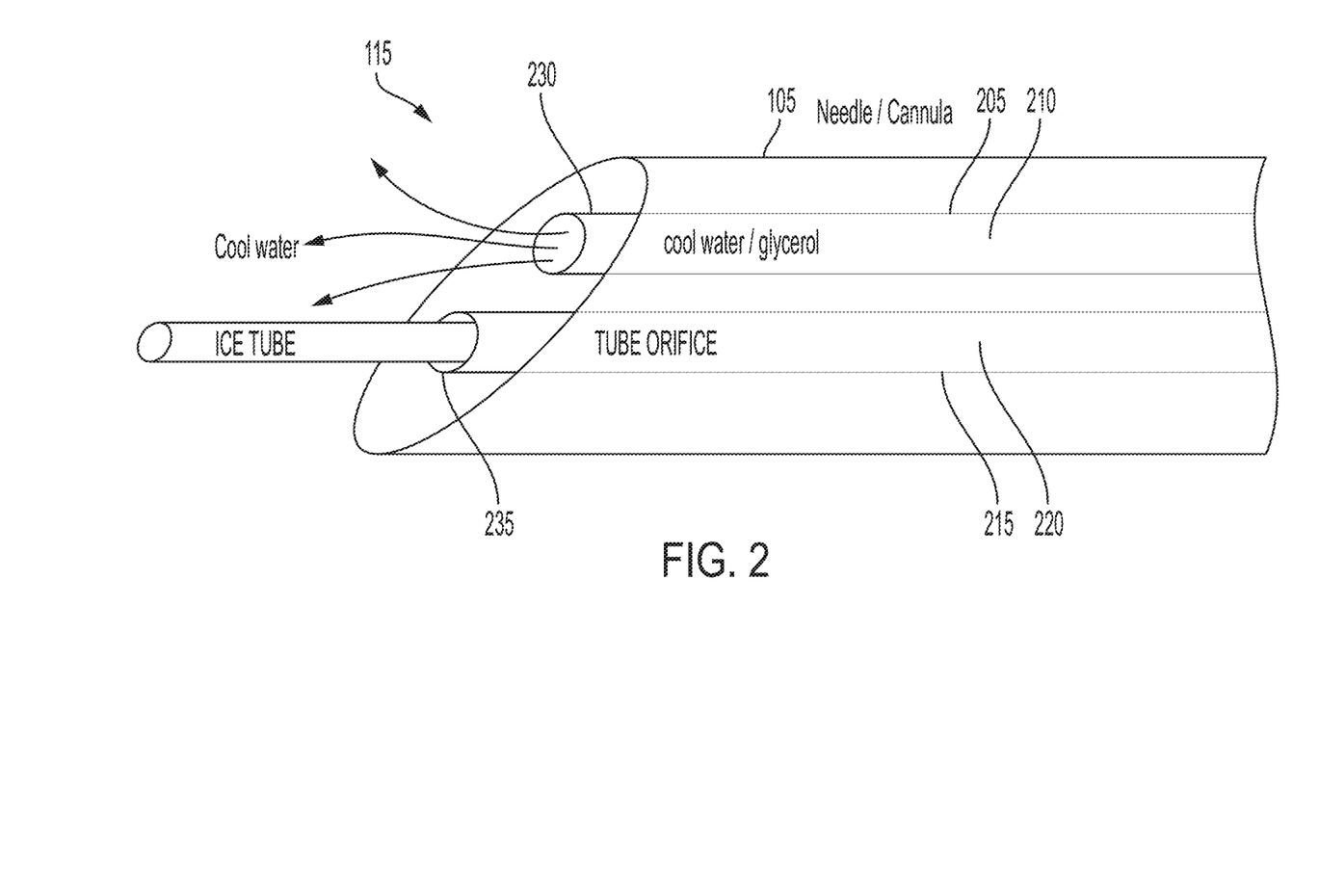
FIG. 2 is a view of a generating end of a point of delivery generation device for forming a cold slurry from liquid water and solid water.

FIG. 2 shows an example of the generating end 115 for making cold slurry from mixing liquid water and solid water. The application cannula 105 houses a first delivery cannula 205 for supplying liquid water 210 (or a liquid mix of water and glycerol) and a second delivery cannula 215 for supplying solid water (ice) 220. The distal end of the first delivery cannula 205 is open and forms a first outlet 230 for the liquid water 210 to exit. The distal end of the second delivery cannula 215 is open and forms a second outlet 235 for the solid water 220 to exit. The outlets 230, 235 are arranged so that the liquid water 210 and the solid water 220 mix together as they exit to form a cold slurry.

Figure 3A:
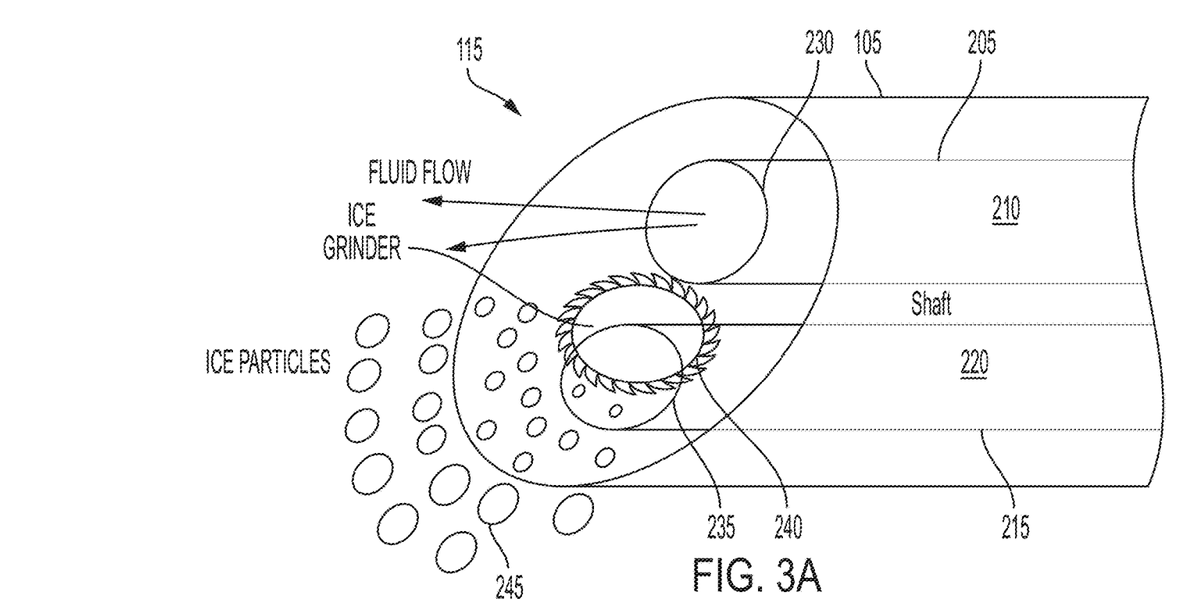
FIG. 3A is a view of a generating end of another point of delivery generation device for forming a cold slurry from liquid water and solid water.
Figure 3B:
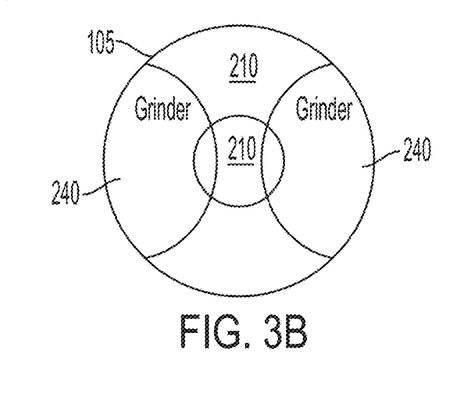
FIG. 3B is a sectional view of the generating end of FIG. 3A.

FIG. 3A shows an example of the generating end 115 for making cold slurry from mixing liquid water and solid water. This example is similar to the one described above with reference to FIG. 2 with the addition of a grinder 240 located in front of the second outlet 235. The arrangement of the grinder 240 with respect to the second outlet 235 is better seen in the cross-sectional view of FIG. 3B. As the solid water 220 emerges from the second delivery cannula 215, the grinder 240 breaks the solid water 220 into particles 245. The liquid water 210 exiting from the first delivery cannula 205 mixes with the particles 245 to form a cold slurry. In another example (not shown), a vibrator can break solid water into particles to make cold slurry at the point of delivery.

Figure 4:
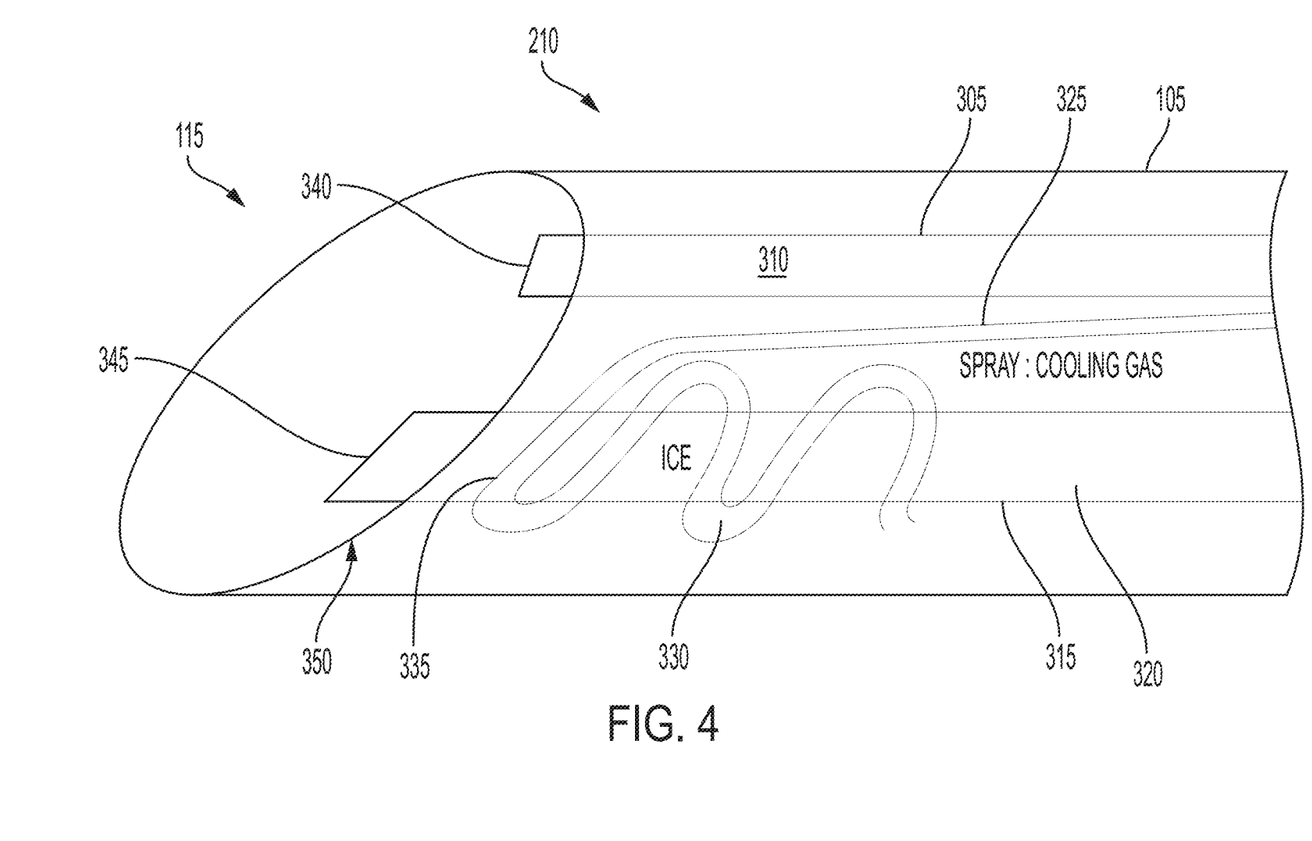

FIG. 4 shows another example of the generating end 115 for making a cold slurry from mixing liquid water and solid water. The application cannula 105 houses a first delivery cannula 305 for providing a first supply of liquid water 310 (or mix of water and glycerol) and a second delivery cannula 315 for providing a second supply of liquid water 320. As shown, the application cannula 105 further includes a gas line 325 for spraying a cooling gas 330 and freezing the second supply of water 320 into solid water 335.

The distal end of the first delivery cannula 305 is open forming a first outlet 340 for the first supply of liquid water 310 to exit. The distal end of the second delivery cannula 315 is open forming a second outlet 345 for the solid water 335 to exit. In front of the second outlet 345, there is a grinder (or vibrator) 350 to break the solid water 335 into particles as it emerges from the second delivery cannula 315. The outlets 340, 345 are arranged so that the first supply of liquid water 310 and the particles of solid water mix together to form a cold slurry.

Figure 5:
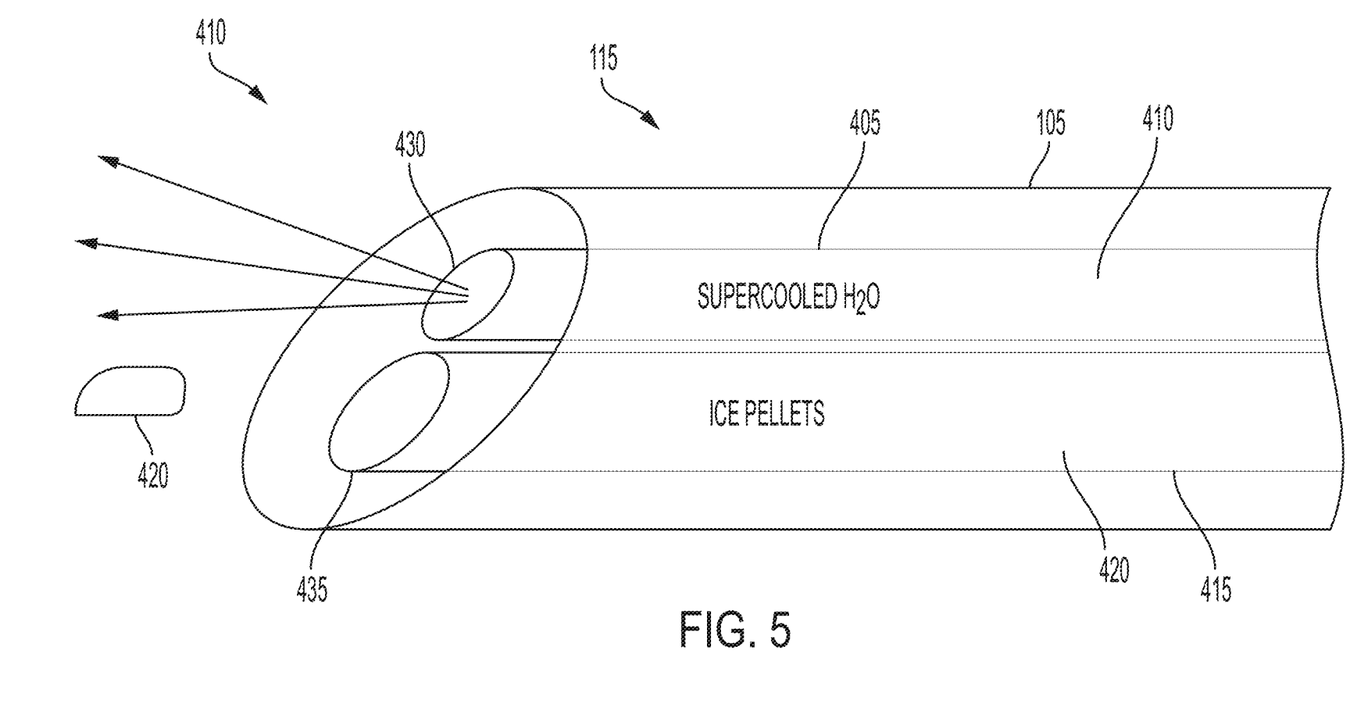
FIG. 5 is a view of a generating end of a point of delivery generation device for forming a cold slurry from supercooled water and ice pellets.

FIG. 5 shows an example of the generating end 115 for making cold slurry from crystalizing supercooled water. The application cannula 105 houses a first delivery cannula 405 for supplying supercooled water 410. Water normally freezes at 273.15 K (0° C. or 32° F.), but it can be "supercooled" at standard pressure down to its crystal homogeneous nucleation at almost 224.8 K (−48.3° C./−55° F.). The supercooling process requires that water be pure and free of nucleation sites. This can be done by processes like reverse osmosis or chemical demineralization. Rapidly cooling water at a rate on the order of 10^6 K/s avoids crystal nucleation and water becomes a glass, i.e., an amorphous (non-crystalline) solid.

The application cannula 105 further houses a second delivery cannula 415 for supplying ice pellets 420, which serves as nucleation sites for the crystallization process. The distal end of the first delivery cannula 405 is open and forms a first outlet 430 for the supercooled water 410 to exit. The distal end of the second delivery cannula 415 is open and forms a second outlet 435 for the ice pellets 420 to exit. The outlets 430, 435 are arranged so that the supercooled water 410 interacts with the ice pellets 420 causing it to crystalize and form a cold slurry.

Figure 6A:
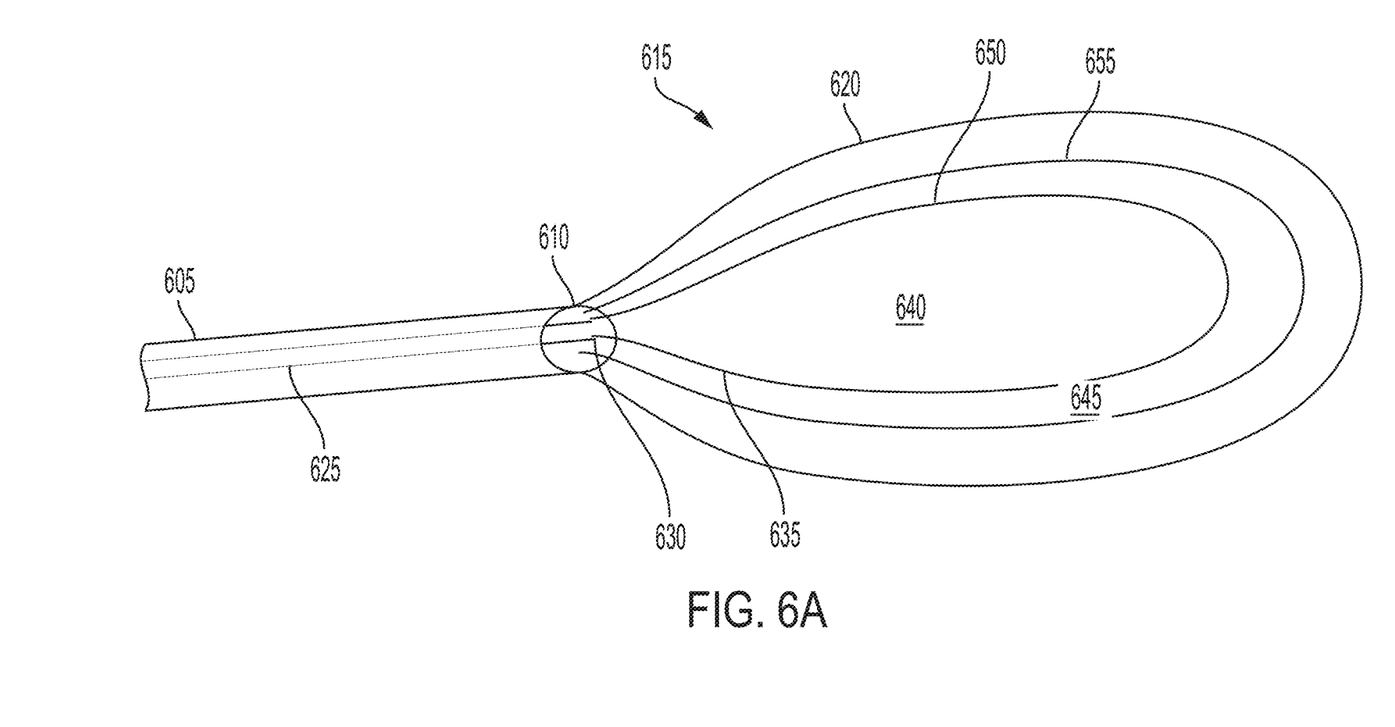
FIGS. 6A and 6B are views of a generating end of a point of delivery generation device for forming a cold slurry inside a balloon.

FIG. 6A shows another example of the point of delivery generation device. The device includes an application cannula 605 that is open at its distal end defining an outlet 610. A generating end 615 includes an outer balloon 620 disposed around the outlet 610. The application cannula 605 is in fluid communication with the interior volume of the outer balloon 620. The application cannula 605 includes a fluid delivery cannula 625. The application cannula 605 and the fluid delivery cannula 625 share a common longitudinal axis and can be said to be coaxial aligned.

The fluid delivery cannula 625 is open at its distal end defining a fluid outlet 630. The generating end 615 further includes an inner balloon 635 disposed around the fluid outlet 630. The fluid delivery cannula 625 is in fluid communication with an interior volume of the inner balloon 635, which is labeled 640 in the figure. The inner balloon 635 is located inside the outer balloon 620. As shown, the inner balloon 635 occupies a portion of the interior volume of the outer balloon 620 leaving a space or gap 645 between an outer wall of the inner balloon 635 (which is labeled 650 in the figure) and an inner wall of the outer balloon 620 (which is labeled 655 in the figure).

To generate a cold slurry at the point of delivery, the application cannula 605 is inserted through a patient's skin and the generating end 615 is advanced to a location at or near a target tissue in much the same manner as described above with reference to FIG. 1. In this example, the outer balloon 620 and the inner balloon 635 are inserted into the patient's body in their uninflated state. The inner balloon 635 is then filled or inflated with a cool fluid, such as mix of cold water and cold glycerol that is supplied through the fluid delivery cannula 625.

Figure 6B:
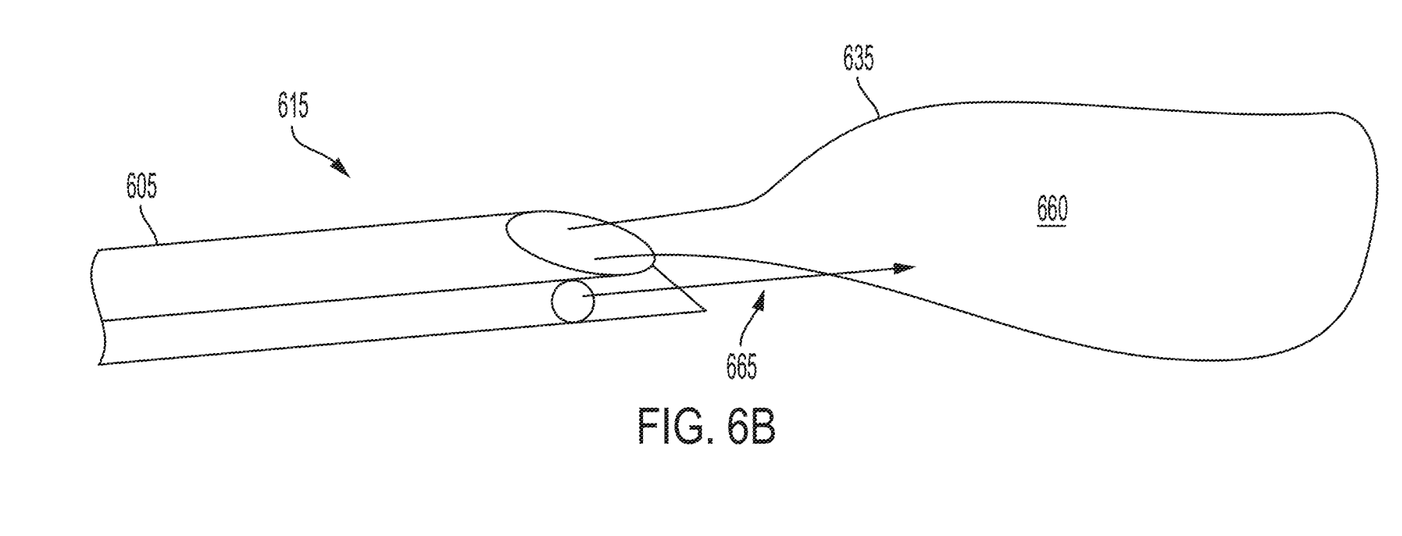

Once the inner balloon 635 is filled with the cool fluid, the outer balloon 620 is filled with a cooling gas or fluid, such as liquid nitrogen. The cooling gas fills the gap 645 between the inner balloon 635 and the outer balloon 620. This causes the cool fluid in the inner balloon 635 to partial freeze and form a cold slurry 660, as shown in FIG. 6B. (For clarity the outer balloon 620 is not shown in FIG. 6B.) The slurry-filled inner balloon 635 can then be used to cool a target tissue. Alternatively, the inner balloon 635 can be ruptured by a retractable puncture needle 665 that extends beyond the application cannula 605 when extended as shown. Rupturing the inner balloon 635 releases the cold slurry 600 at or near the target tissue.

Figure 7:
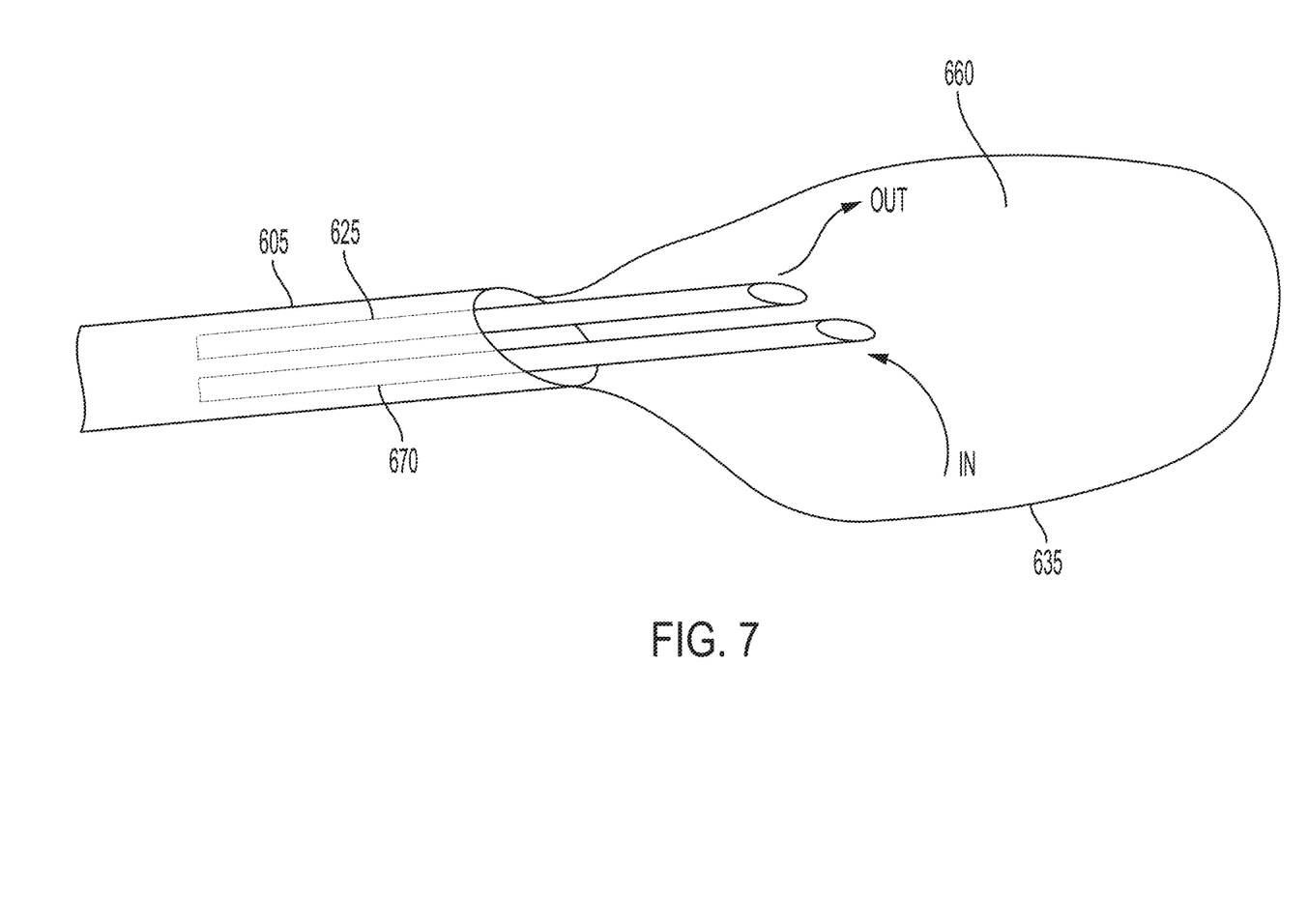
FIG. 7 is a view of a point of delivery generation device for generating and replenishing cold slurry.

FIG. 7 shows another example of the point of delivery generation delivery device for generating and replenishing cold slurry. This example is similar to the one described above with reference to FIG. 6 with the addition of a fluid return cannula 670. (For clarity the outer balloon 620 is not shown in FIG. 7.) The fluid return cannula 670 is housed within the application cannula 605 together with the fluid delivery cannula 625, as shown. The fluid return cannula 670 removes cold slurry from the inner balloon 635 that is no longer at the desired temperature. Replenishing the "old" cold slurry with "fresh" cold slurry in this manner can accommodate for the eventually melting of cold slurry. This approach is particular useful for a treatment that requires a long period of cooling.

Figure 8:
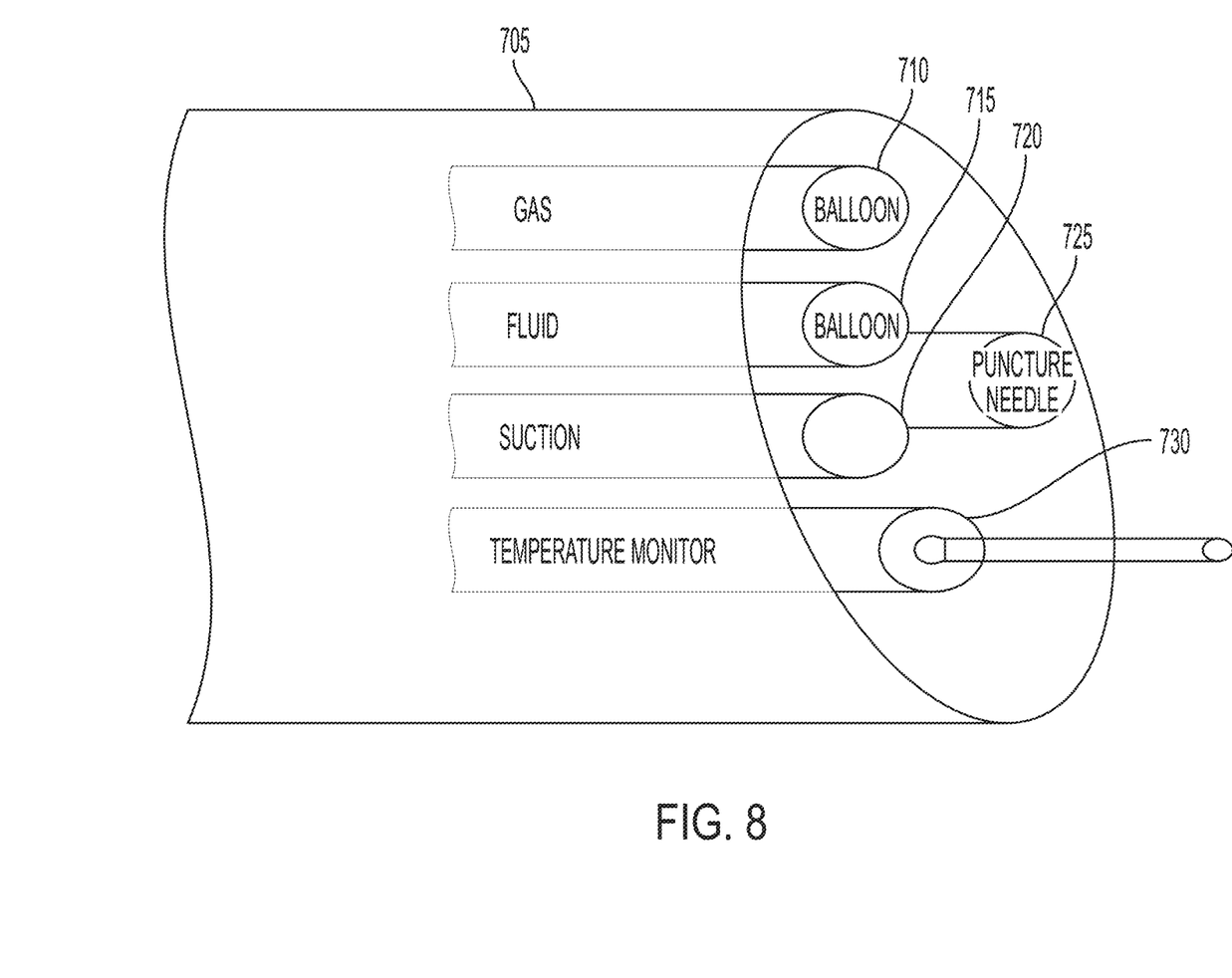
FIG. 8 is a view of a point of delivery generation device having multiple working channels.

FIG. 8 shows an example point of delivery generation device having multiple cannulas or "working channels" to control the functions described above with reference to FIGS. 6A, 6B, and 7. The device includes an application cannula 705. The application cannula 705 houses a gas delivery cannula 710, a fluid delivery cannula 715, and a fluid return cannula 720, to continuously generate and replenish cold slurry, as described above with reference to FIGS. 6A and 7. The application cannula 705 can also include a retractable puncture needle 725 to rupture a balloon filled with cold slurry, as described above with reference to FIG. 6B. The application cannula 705 can further have a cold slurry temperature monitor 730 for measuring the temperature of the cold slurry.

What is claimed is:

1. A method of making a cold slurry at or near a target tissue underneath a subject's skin, the method comprising:
   delivering a first component to a target tissue underneath a subject's skin;
   delivering a second component to the target tissue; and
   forming a cold slurry at or near the target tissue from an interaction between the first component and the second component.

2. The method of claim 1, wherein the steps of delivering and the step of forming the cold slurry are carried out continuously.

3. The method of claim 1, wherein the first component is a liquid water and the second component is solid water.

4. The method of claim 3 further comprising breaking the solid water into particles of solid water at or near the target tissue.

5. The method of claim 3 further comprising forming the solid water by freezing liquid water at or near the target tissue.

6. The method of claim 1, wherein the first component is supercooled water and the second component is pellets of solid water; and
   wherein the interaction is crystal nucleation of the supercooled water caused by the pellets of solid water.

7. The method of claim 1, wherein the first component is liquid water contained in an inner balloon and the second component is a cooling fluid surrounding the inner balloon and contained within an outer balloon; and
   wherein the interaction is heat transferring from the liquid water to the cooling fluid.

8. The method of claim 7 further comprising puncturing the inner and outer balloons to release the cold slurry at or near the target tissue.

9. A device for making a cold slurry at or near a target tissue underneath a subject's skin, the device comprising:
   a first cannula for delivering a first component to a target tissue underneath a subject's skin, the first cannula comprising a first open distal end and first longitudinal axis extending from the first open distal end;
   a second cannula for delivering a second component to the target tissue, the second cannula comprising a second open distal end and a second longitudinal axis extending from the second open distal end, the second longitudinal axis aligned with the first longitudinal axis;
   wherein the first open distal end is proximate to the second open distal end for forming a cold slurry at or near the target tissue from an interaction between the first component and the second component.

10. The device of claim 9, wherein the first component is liquid water and the second component is solid water.

11. The device of claim 10 further comprising a grinder disposed about the second open distal end to break the solid water into particles of solid water at or near the target tissue.

12. The device of claim 10 further comprising a vibrator disposed about the second open distal end to break the solid water into particles of solid water at or near the target tissue.

13. The device of claim 10 further comprising a third cannula extending along the second cannula for carrying a cooling gas to form the solid water from liquid water at or near the target tissue.

14. The device of claim 9, wherein the first component is supercooled water and the second component is pellets of solid water; and
   wherein the interaction is crystal nucleation of the supercooled water caused by the pellets of solid water.

15. The device of claim 9 further comprising:
an inner balloon disposed around the first open distal end of the first cannula, the inner balloon comprising an outer surface and a volume in fluid communication with the first cannula to receive the first component;
an outer balloon disposed around the second open distal end of the second cannula, the outer balloon comprising an inner surface and a volume in fluid communication with the second cannula to receive the second component; and
wherein the outer surface of the inner balloon and the inner surface of the outer balloon form a space for the interaction between the first and second components to occur, and form the cold slurry inside the inner balloon.

16. The device of claim 15, wherein the first component is a mixture of water and glycerol; and
wherein the second component is a cooling gas.

17. The device of claim 15 further comprising a puncture needle extending along the second cannula and movable between an extended position and a retracted position; and
wherein the puncture needle in the extended position breaks the inner balloon and the outer balloon, and releases the cold slurry at or near the target tissue.

18. The device of claim 9 further comprising a temperature sensor extending beyond the first and second open distal ends to measure the temperature of the cold slurry made at or near the target tissue.

19. The device of claim 9, wherein the first and second cannulas each have a size and shape suitable for inserting through the subject's skin.

* * * * *